(12) United States Patent
Harwood et al.

(10) Patent No.: US 7,599,802 B2
(45) Date of Patent: Oct. 6, 2009

(54) V-LIFE MATCHING AND MATING SYSTEM

(76) Inventors: Evan Harwood, 804 Longview Ave., North Woodmere, NY (US) 11581; Ian Grody, 1000 Island Blvd., Unit 1807, Aventura, FL (US) 33160

( * ) Notice: Subject to any disclaimer, the term of this patent is extended or adjusted under 35 U.S.C. 154(b) by 843 days.

(21) Appl. No.: 10/865,094

(22) Filed: Jun. 10, 2004

(65) Prior Publication Data

US 2005/0278125 A1    Dec. 15, 2005

(51) Int. Cl.
*G06F 19/00*    (2006.01)
*G06F 17/00*    (2006.01)
*G06N 3/00*    (2006.01)

(52) U.S. Cl. .............. 702/20; 463/30; 706/13

(58) Field of Classification Search ............ None
See application file for complete search history.

(56) References Cited

U.S. PATENT DOCUMENTS

| | | | |
|---|---|---|---|
| 5,086,394 A | 2/1992 | Shapira | 364/419 |
| 5,681,046 A | 10/1997 | Lawrence | 273/459 |
| 5,920,845 A | 7/1999 | Risenberg | 705/1 |
| 5,963,951 A | 10/1999 | Collins | 707/102 |
| 6,052,122 A | 4/2000 | Sutcliffe et al. | 345/331 |
| 6,061,681 A | 5/2000 | Collins | 707/5 |
| 6,243,375 B1 | 6/2001 | Speicher | 370/352 |
| 6,282,515 B1 | 8/2001 | Speicher | 705/14 |
| 6,594,502 B1 | 7/2003 | Koester | 455/550 |
| 2002/0082077 A1* | 6/2002 | Johnson et al. | 463/30 |
| 2002/0094851 A1* | 7/2002 | Rheey | 463/1 |
| 2004/0053690 A1* | 3/2004 | Fogel et al. | 463/31 |
| 2005/0112684 A1* | 5/2005 | Holzle | 435/7.1 |

OTHER PUBLICATIONS

Herz, J.C. The New York Times (Dec. 9, 1999) Game Theory; Virtual Parenthood, Complete with Mess, pp. 1-3 (internet pages).*
Sims, K. Computer Graphics: Annual Conference Series (SIGGRAPH '94 Proceedings), Jul. 1994, pp. 15-22.*
Cercueil et al. The Journal of Heredity (2002) vol. 93, pp. 458-459.*

* cited by examiner

*Primary Examiner*—Lori A Clow
(74) *Attorney, Agent, or Firm*—Jack Schwartz & Associates, PLLC

(57) ABSTRACT

A system for producing virtual offspring including means for acquiring genetic material from users. The system further includes means for analyzing the acquired genetic material for determining at least one trait corresponding to the genetic material. A user database stores user data representing the at least one trait for each respective one of the users. A search mechanism allows the users to search the stored user data for users having at least one desirable trait. The system also includes means for virtually combining genetic material of a first user with genetic material of a selected second user for producing a virtual offspring. The first user inputs the at least one desirable trait into the searching mechanism and the searching mechanism retrieves users having the at least one input desired trait. The virtual combining means combines said genetic material from said first user and a selected one of the users having the at least one input desired trait to produce a virtual offspring from genetic material of each of the first and second users.

23 Claims, 9 Drawing Sheets

V-LIFE MATCHING AND MATING SYSTEM

BACKGROUND OF THE INVENTION

1. Field of the Invention

The present invention relates generally to a match-making system and, more specifically, to a system that obtains and utilizes DNA from users of the system in order for a first user to select the DNA of a second user having desired traits. Thereafter the system virtually combines the DNA of the first and second users in order to produce virtual offspring. The users are then able to rear and monitor the virtual child.

2. Description of the Prior Art

Numerous matching systems are present in the prior art. Typical prior art matching systems are described in U.S. Pat. Nos. 5,086,394; 5,681,046; 5,920,845; 5,963,951; 6,052,122; 6,061,681; 6,243,375; 6,282,515 and 6,594,502.

One such prior art system requires users to submit data about themselves as well as data about a desired mate. This data is then stored in a personal device which the users can take with them. The personal devices are connected to a local control unit which receives information from the personal devices within a specified area and compares all received information in order to determine if a match exists. If a match exists the control unit transmits match signals to the personal devices of the matched users and the users approach and meet at the local control unit.

Additionally, there are matching "games" whereby users answer a plurality of questions by giving a numerical rating as to the importance each characteristic. The numerical ratings are averaged and related to a compatibility scale to determine if a match exists. Other games are known wherein the users are given observable tags including preferences thereon. The users are able to interact and submit preferences regarding the people they just met. A computer queries the preferences and determines a match list which includes information for setting up additional meetings between matched users.

Other known matching systems include a database that stores user information and preferences associated with the user information. The database repeatedly is searched for a potential match whereby each successive search utilizes a less restrictive search criteria until a match is found. This database is remotely accessible via a telephone or internet and allows user to store messages about themselves which are selectively displayable to other users.

While these matching systems may be suitable for the purposes for which they were designed, they would not be as suitable for the purposes of the present invention, as hereinafter described.

Additionally, extracting DNA from human cells is also well known. Specifically, usable DNA for genetic sequencing can be obtained by taking a swab of the inside of the cheek of a user. When the cheek is swabbed with a cotton swab, epithelial cells (buccal cells) are removed and the cells adhere thereto. The cells on the swab can be lysed in order to remove the DNA contained therein. Typically, the cells are put through a digestion process using a proteinase enzyme which breaks down the cellular components so that the DNA contained in the nucleus can be isolated for later use. Upon completion of the digestion process, the nucleic acids are stabilized and are put through a plurality of washes wherein any impurities present from the digestion process are removed. Thereafter, the DNA is eluted in water or a low-salt solution. This procedure yields DNA that is suitable for a plurality of molecular processes including forensic analysis, diagnostic testing and sequencing.

Upon elution of the DNA as described above, it is important to ensure that there is enough of the DNA sample present for adequate sequencing thereof. A preferred method of producing large quantities of DNA sequences (amplification) for analysis is using a polymerase chain reaction (PCR) technique. This technique requires knowledge of part of the sequence to be amplified for synthesis of two oligonucleotide which bind to a single strand of denatured DNA for amplification thereof using the Taq polymerase enzyme. Taq polymerase is an enzyme that extends the length of a DNA strand from the primer using nucleotides as building blocks. The PCR reaction is run in cycles. A single cycle includes the following steps. The DNA must first be denatured by heating it for a predetermined amount of time until the DNA separates into a single strand. The temperature is then reduced so that the oligonucleotide primers can bind to the denatured DNA. Thereafter, the temperature is increased so that the Taq Polymerase can extend the length of the DNA strand. Generally this process is automated so that a plurality of cycles can be completed thereby significantly increasing the amount of target DNA.

Once a sufficient amount of the target DNA is present, the DNA can be sequenced. A common method of sequencing DNA is through an elongation of a single strand of DNA using a polymerase enzyme similar to the PCR described above. However, in addition to a primer, deoxynucleotides, and the DNA polymerase, a limited number of dideoxyneleotides are inserted as well. The dideoxynucleotide is at least one of Adenine, Thymine, Cytosine, and Guanine and lacks a hydroxyl group at the 3' end which prevents further synthesis of the DNA strand. For this procedure to work properly, there must be four separate simultaneous reactions wherein each one of the reaction has a different dideoxynucleotide. Therefore, within an individual reaction a plurality of different sized DNA strands are synthesized each having same dideoxynucleotide at the 3' end. In order to obtain the full sequence the, the DNA fragments from each of the four reactions are aligned adjacently and separated by gel electrophoresis. This produces a ladder map in four lanes which can be read from top to bottom to correctly obtain the sequence of the target DNA. Additionally, sequencing machines exists that use four different colored fluorescent dyes which produce a colored pattern of peaks from which the sequence can be determined.

SUMMARY OF THE PRESENT INVENTION

The present invention relates generally to a match-making system and, more specifically, to a system that obtains and utilizes DNA from users of the system in order for a first user to select the DNA of a second user having desired traits. Thereafter the system virtually combines the DNA of the first and second users in order to produce virtual offspring. The users are then able to rear and monitor the virtual child.

A primary object of the present invention is to overcome the shortcomings of prior art match-making systems by providing users the ability to choose potential matches based on traits identified from user's DNA.

Another object of the present invention is to obtain a sample of DNA from a user for sequencing thereof. Thereafter, the sequence is compared with a known sequence which corresponds to a plurality of phenotypic and genotypic traits. When a portion of the user's sequence matches a portion of the known sequence, the trait is stored in a searchable database. This procedure is repeated until the user's sequence has been matched with all known sequences that correspond to human traits.

A further object of the present invention is to provide match-making system wherein each user of the system can search the trait database for traits that user find to be desirable in a potential mate. Specifically, the user is able to enter a plurality of traits in a form based computer application which queries stored entries and produces a list of potential matches. The matches come from registered users of the system that have had their DNA sequenced to produce a trait list. The system returns a list of potential matches based on the input traits. The requesting user may then further narrow or expand the search until the user finds an ideal match. Upon finding an ideal match, the requesting user may be able to view all of the user's traits that were identified in when the DNA was sequenced.

An additional object of the present invention is to provide a matching system wherein each user's contact information is kept confidential until there is mutual agreement between both the requesting user and desired user to contact one another. This ensures privacy and prevents misappropriation of information obtained during a search.

Still another object of the present invention is to provide means for creating a virtual child by combining DNA from two consenting users of the system. The system allows for a virtual offspring of two users to be formed by combining the genetic traits of each user to form a single virtual offspring that will express the combined traits. Preferably, the traits are combined using an algorithm that takes into account various external factors affecting each traits including but not limited to dominance, recessiveness, sex-linkage. For each trait that is combined a unique algorithm based on the external factors associated with that particular trait is employed. This process is preferably combined in a software application that runs every algorithm and outputs a single list of traits to be expressed by the offspring. Alternatively, an algorithm can be employed to simulate conception whereby the DNA of each user will virtually undergo meiosis to produce a gamete for combination therebetween. Thereafter, a second algorithm is employed, which includes external factors as discussed above to determine, upon combination of the genetic material from each gamete, which trait will be expressed.

Yet a further object of the present invention is to provide a virtual world in which each virtual offspring can be raised. The user's can selectively determine whether or not to participate in at least one of a fully automated virtual world, and a completely interactive virtual world. In the fully automated virtual world, the only active participants are the user's and the virtual child. In the completely interactive virtual world, only the backbone structure is automated and each user and their virtual child are active participants and are able to interact with other virtual parents and their respective virtual children.

Another object of the present invention is to provide a plurality of virtual worlds wherein each virtual world functions on a different time scale. Preferably, one virtual world operates in real time and another operates at an accelerated time to allow the virtual child to be raised at a quicker pace.

Yet a further object of the present invention is to provide a virtual orphanage to place any unwanted virtual children therein. User's who do not wish to find a potential mate to produce a virtual child can search the virtual orphanage to adopt a virtual child. Upon adopting a virtual child the user and virtual child can join a fully automated virtual world or the interactive virtual world.

Still another object of the present invention is to provide means for transporting the virtual child on a portable electronic device.

The foregoing and other objects and advantages will appear from the description to follow. In the description reference is made to the accompanying drawings, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWING FIGURES

In order that the invention may be more fully understood, it will now be described, by way of example, with reference to the accompanying drawing in which.

Figure 1:
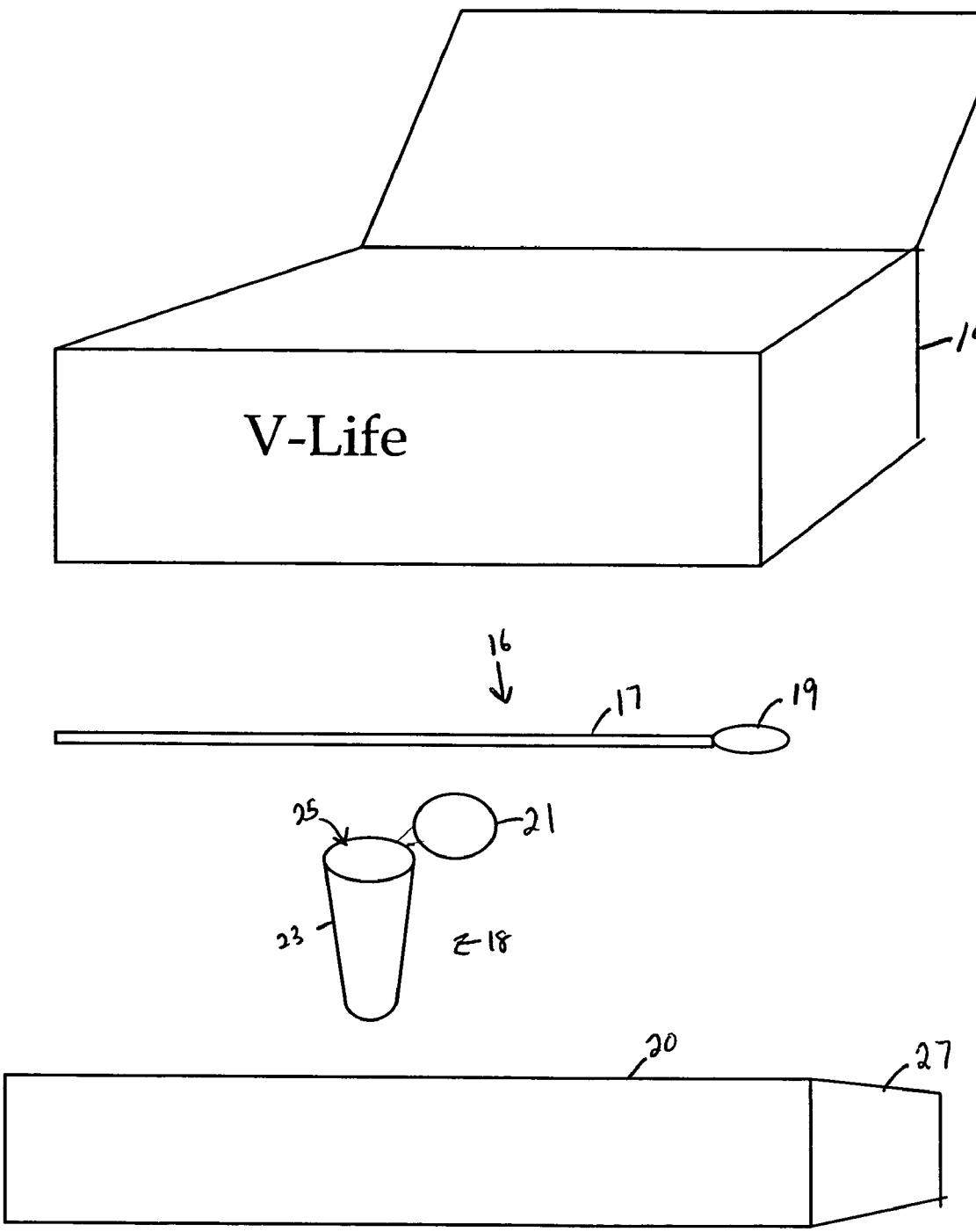
FIG. 1 is an illustrative view of the V-Life DNA kit for acquiring a DNA sample from a user of the system.

The foregoing and other objects and advantages will appear from the description to follow. In the description, reference is made to the accompanying drawing, which forms a part hereof, and in which is shown by way of illustration specific embodiments in which the invention may be practiced. These embodiments will be described in sufficient detail to those skilled in the art to practice the invention, and it is to be understood that other embodiments may be utilized and that structural changes may be made without departing from the scope of. In the accompanying drawings, like reference characters designate the same or similar parts throughout the several views.

DETAILED DESCRIPTION OF THE PREFERRED EMBODIMENTS

The following discussion describes in detail one embodiment of the invention and several variations of that embodiment. This discussion should not be construed, however, as limiting the invention to those particular embodiments. Practitioners skilled in the art will recognize numerous other embodiments as well. For a definition of the complete scope of the invention, the reader is directed to the appended claims.

Turning now descriptively to the drawings, in which similar reference characters denote similar elements throughout the several views, FIGS. 1 through 9 illustrate a mating and matching system of the present invention indicated generally by the numeral 10.

FIG. 1 is an illustrative view of the V-Life DNA kit for acquiring a DNA sample from a user of the system. The V-life mating and matching system 10 (hereinafter, the system) allows users submit their genetic material for sequencing thereof. From the sequence obtained, the traits associated with each user's genetic sequence are stored in a trait database. The trait database is then selectively searchable by other users who can search in order to find a potential matching user having traits that the searching user finds desirable. The searching user is then able to select at least one matching user so that the system 10 can selectively virtually combine the traits of both the searching user and the matching user to produce a virtual child. The user's are then able to choose how to selective raise the virtual child.

Shown in FIG. 1 is how each user of the system 10 is to submit their genetic material for sequencing and analysis thereof. Upon a user registering with the system 10, a genetic kit 12 is sent to and received by the user. The kit 12 is preferably contained in a box 14. However, the kit 12 may be sent and received in any manner which allows the contents of the kit 12 to be received by the user without incurring any damage thereto. It is also preferable that the box 14 include a printed advertisement of the system 10 on the outside thereof. Contained in the box 14 is a swab 16, a vile 18 and an envelope 20. The swab 16 is preferably formed from a staff 17 having a cotton tip 19 positioned at a distal end thereof. The vile 18 includes a body 23 with a circular opening 25 at first end thereof. A lid 21 is removeably connected to the body 23 and selectively covers the opening 25. The envelope 20 preferably has padding along the inner surface thereof for preventing any damage from occurring to any objects contained therein. A flap 27 is positioned at a first distal end of the envelope for selectively sealing any contents therein.

The process of obtaining the genetic material of a user using the contents of the kit 12 will be discussed hereinafter. In order to obtain the genetic material from the user, the user grips the staff 17 and runs the cotton tip 19 along the inside of his/her cheek. This allows the cotton tip 19 to collect epithelial cells thereon. The swab 16 then must be transferred to a lab employed by the system 10. The user inserts the cotton tip 19 of the swab 16 through the opening 25 of the vile 18 so that the cotton tip 19 is positioned within the body 23 of the vile 18. The user then breaks off a portion of the staff 17 that extends out from the body 23 through the opening 25 of the vile 18. The lid 21 is secured over the opening 25 thereby creating an airtight seal. The user then inserts the sealed vile 18 in the envelope 20 and seals the envelope 20 using the flap 27. Preferably, the envelope is a postage paid envelope having an address printed thereon thereby ensuring that user's epithelial cells are received by a desired laboratory. As discussed hereinabove in the background section of the present application, the genetic material is then eluted from the epithelial cells contained on the cotton tip 19 of the swab 16 in a known manner.

It is preferable that the box 14 in which the kit 12 is contained, includes printed instructions detailing the above process by which the DNA of the respective user is acquired. Additionally, the printed instructions may include information about the process of how the DNA is actually eluted from the cotton swab 19 as well as a detailed statement as to how the user's privacy is to be maintained. It is well known that genetic material contains very specific information about the user from which it is obtained and thus it is important to maintain the strictest level of privacy so as to allow very selective access to the information to prevent any mishandling or misappropriation thereof.

Figure 2:
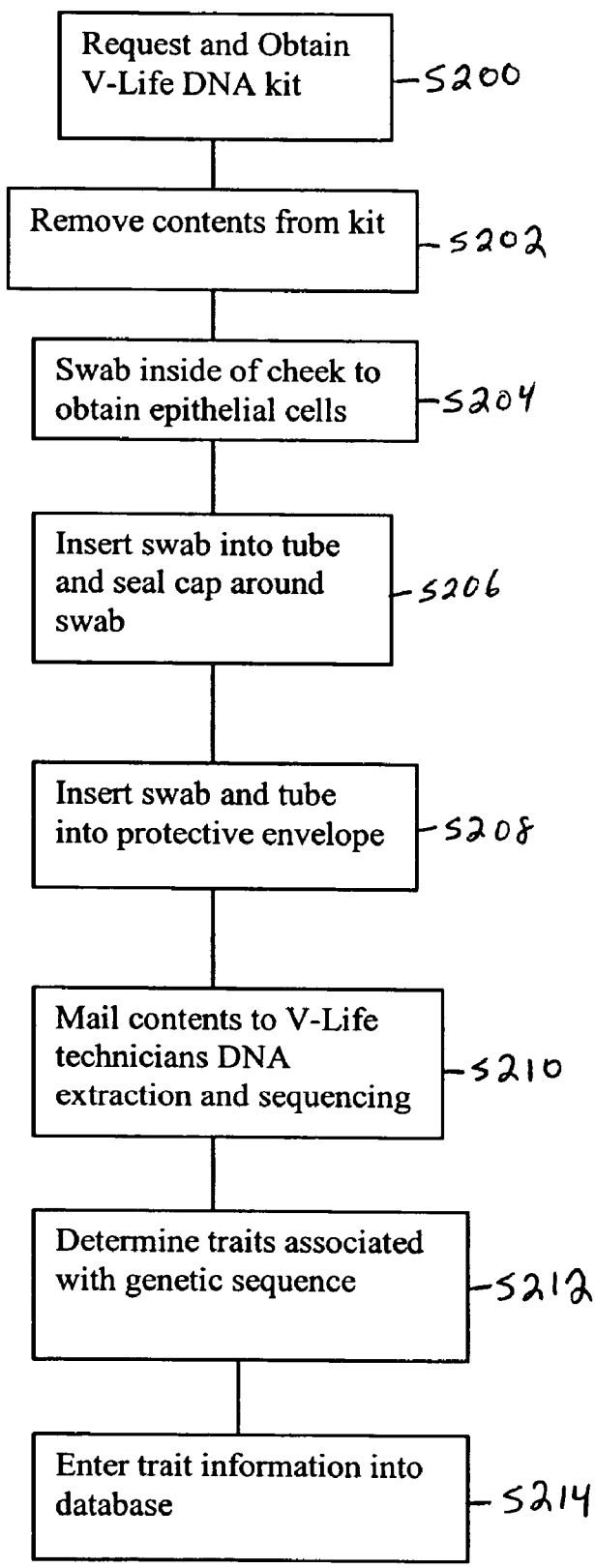
FIG. 2 is a flow diagram detailing the process of obtaining DNA from a user and acquiring the sequence thereof.

FIG. 2 is a flow diagram detailing the process of obtaining DNA from a user and acquiring the sequence thereof. As discussed above with respect to FIG. 1, the system 10 uses information obtained from actual DNA in order to provide a mating and matching system. As shown in step S200, a user who desires to participate in the system requests and receives a V-life DNA kit from V-life. The kit 12 is shown and discussed above in FIG. 1. Thereafter, the contents of the kit 12 are removed from the box 14 as shown in step S202 and the cotton tip 19 of the swab is run along the inside of the user's cheek to collect epithelial cells as discussed in step S204. Step S206 requires the user to insert the cotton tip 19 of the swab 16 into the vile 18 and seal the lid 21 in order to enclose the tip 19 having the epithelial cells therein. The vile 18 is then inserted in the envelope 20 as shown in step S208 and the contents of the envelope 20 are transferred, preferably via courier or postal service, to technicians at the V-Life lab as described in step S210. In step S212, the technicians at the V-life lab elute the DNA from the epithelial cells in order to sequence the DNA and determine the traits which correspond to the sequenced DNA. The manner in which the DNA is eluted from the cotton tip 19 of the swab 16 is known and is not the subject of the present patent application. Upon determining the traits which correspond to the user's DNA, a user record is created in a trait database and each trait associated with the user's DNA is entered and stored under the created user record as shown in step S214.

Figure 3:
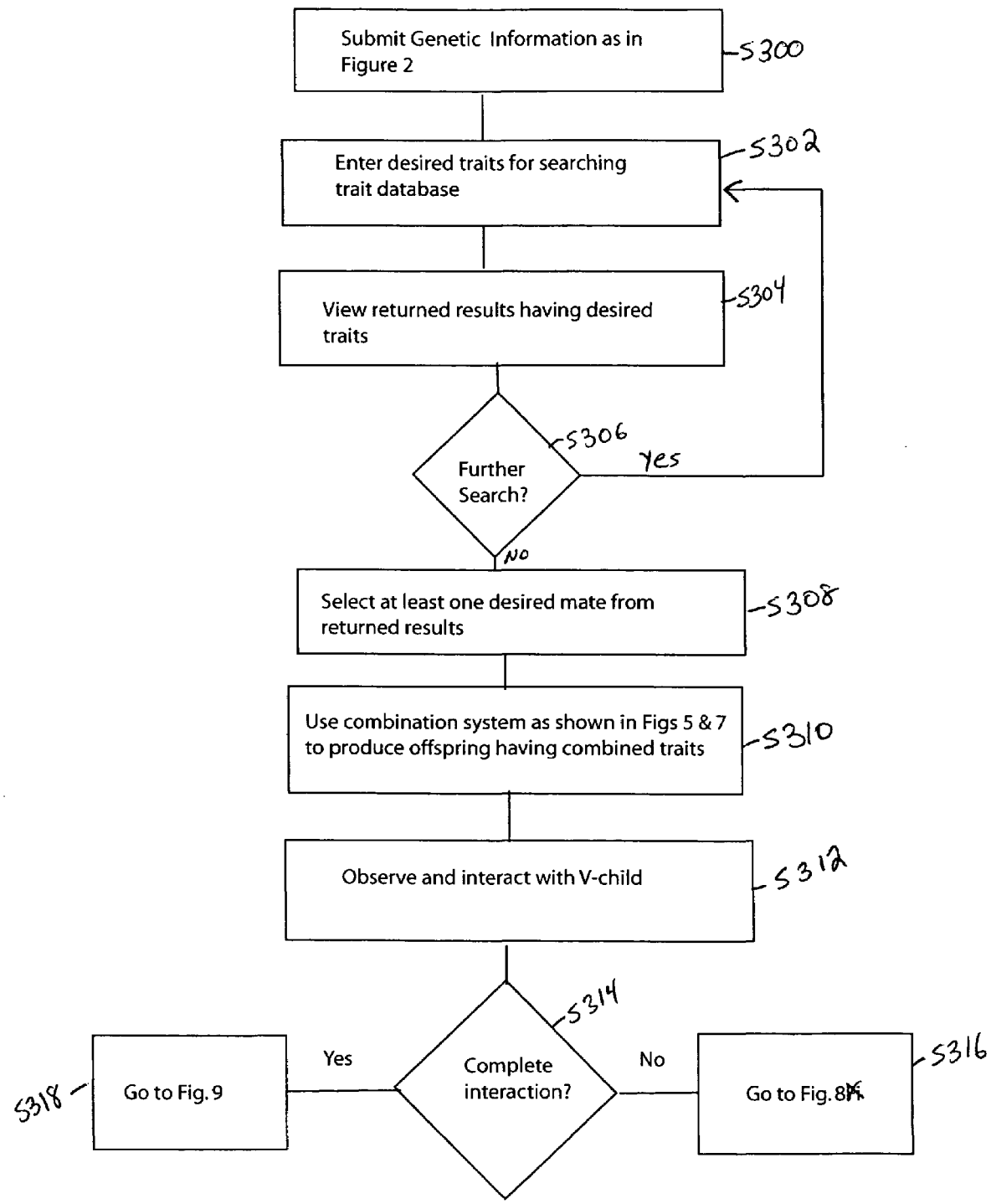
FIG. 3 is a flow diagram detailing how the V-life system functions.

FIG. 3 is a flow diagram detailing how the V-life system 10 functions. The first step in using the V-Life system, as shown in step S300, is to submit and analyze the genetic material as discussed hereinabove with respect to FIGS. 1 and 2. Upon the genetic material being analyzed and generation of a user record containing trait information, the user is able to continue to use the V-life system 10 of the present invention.

For the following steps discussed below with respect to FIG. 3 and throughout the remainder of the description, it is important to note that all the user's of the system inherently have the ability to be a "searching user" as well as a "matching user". However for purposes of clarity, the description will continue from a single user's perspective even though it is preferable to have a plurality of users.

Upon completion of step S300, the user becomes a searching user. The searching user enters traits which are found to be desirable in a potential mate as shown in step S302. For example, the searching user may enter "blue eyes" and "blonde hair". These traits are merely exemplary and stated to illustrate the point of the system 10 of the present invention. The traits include phenotypic traits which are outwardly expressed and visible to other people, such as eye color, and genotypic traits which are not visibly seen by another person, such as being a carrier for sickle-cell anemia. The searching user is able to insert any known traits that are recognized by the system 10 of the present invention. Preferably, the system will provide an updateable list to each user of known traits that are searchable. This list of known traits will be expanded as further research uncovers a genetic sequence that corresponds to a human trait. Furthermore, if additional genetic sequences are uncovered which correspond to a previously identified trait, those genetic sequences will be used to screen all user samples to determine if the user possesses that sequence and the trait associated therewith. It is also preferable that the user samples are regularly re-analyzed in order to add additional traits to the respective user's record in the trait database, thereby allowing the search to be as accurate as possible.

Additionally, the system includes a user feedback system whereby each user can selectively choose to provide additional information about themselves. This additional information includes but is not limited to physical attributes, preferences, likes, dislikes and talents. This list of additional information is described for purposes of example only and the additional information entered by the user in the user feedback system may include any item of information about the user. The data entered by the user into the feedback system is stored in a user feedback database which is linked to the user's genetic information. The searching user can also search for matching users by entering items of additional information that are desirable characteristics. However, as will be discussed hereinafter, the user feedback system will merely be a search aid to assist the searching user in locating a matching user. The search capability of the system 10 may be at least one of a keyword search system and a Boolean search system.

Thereafter, in step S304, the searching user is able to review the results obtained from the search described in step S302. The returned results will display information about the traits of each of the users who correspond to the returned results as well as any information contained in the user feedback system. The searching user will not be provided any identification information about any of the users whose results were returned in the search. The returned results may include all identifiable traits possessed by the user beyond the traits input in the initial search from step S302. This allows the user to selectively determine if the returned result may be a potential match, hereinafter known as a "matching user".

The user then must decide in step S306 whether or not an additional search is required. If the searching user is not happy with the results returned from the search, the searching user is returned to step S302 in order to further tweak the search parameters. This may include at least one of adding additional traits and removing a previously entered trait as well as additional information items. Upon tweaking the search, the searching user then repeats step S304 as described above.

If the searching user does not require an additional search as in step S306, then the searching user proceeds to step S308 wherein the searching user selects at least one desired mate. Upon selecting at least one desired mate, the user then begins a matching process. The matching process is preferably performed by the system 10 in order to maintain the matching user's privacy. The system 10 notifies the matching user that a searching user has chosen the matching user to produce a virtual child. The matching user is provided with the traits possessed by the searching user in order to make a determination as to whether or not the matching user wants to produce a virtual child with the searching user. Upon the matching user deciding to proceed with producing a virtual child with the searching user, the matching and searching users proceed to step S310. The users can also selectively determine to provide the other user with identification information. Alternatively, the system 10 may be configured so as only require the knowledge and consent of the searching party to produce a virtual offspring. If the system 10 is configured in this manner, no identification information is exchanged between the parties and only the matching user's genetic information is provided for virtual combination with the searching user's genetic information to produce a virtual child. Furthermore, the users of the system can contact one another prior to deciding whether or not to produce a virtual child. Additionally, the users can selectively determine if they want to meet one another prior to producing a virtual child.

In step S310, a combination system, such as the ones described hereinafter with specific reference to FIGS. 5 and 7, will be used to combine the genetic information of the searching user with the genetic information of the matching user in order to produce a virtual offspring. The combination system may be at least one of a trait based combination system as shown hereinafter in FIG. 5 and a virtual gamete combination system as shown hereinafter in FIG. 7. The system 10 of the present invention may include either the trait based combination system or the virtual gamete combination systems. Alternatively, the system 10 may include both combination system thereby presenting a choice to the user(s) as to which combination system will be utilized in step S310.

Upon using one of the combination systems in step S310, the searching user and the matching user are able to observe and interact with the produced virtual child in a virtual world as shown in step S312. The user(s) must then decide in step S314 whether or not there will be complete interaction. If the user(s) decide they do not want complete interaction then the virtual child will be raised automatically as shown in step S316. Step S316 directs the user to a fully automated virtual world which will be discussed hereinafter with specific reference to FIG. 8. However, should the user(s) want complete interaction as discussed in step S314, the user(s) are directed to step S318. Step S318 directs the user to a completely interactive world which will be described hereinafter with specific reference to FIG. 9.

Figure 4:
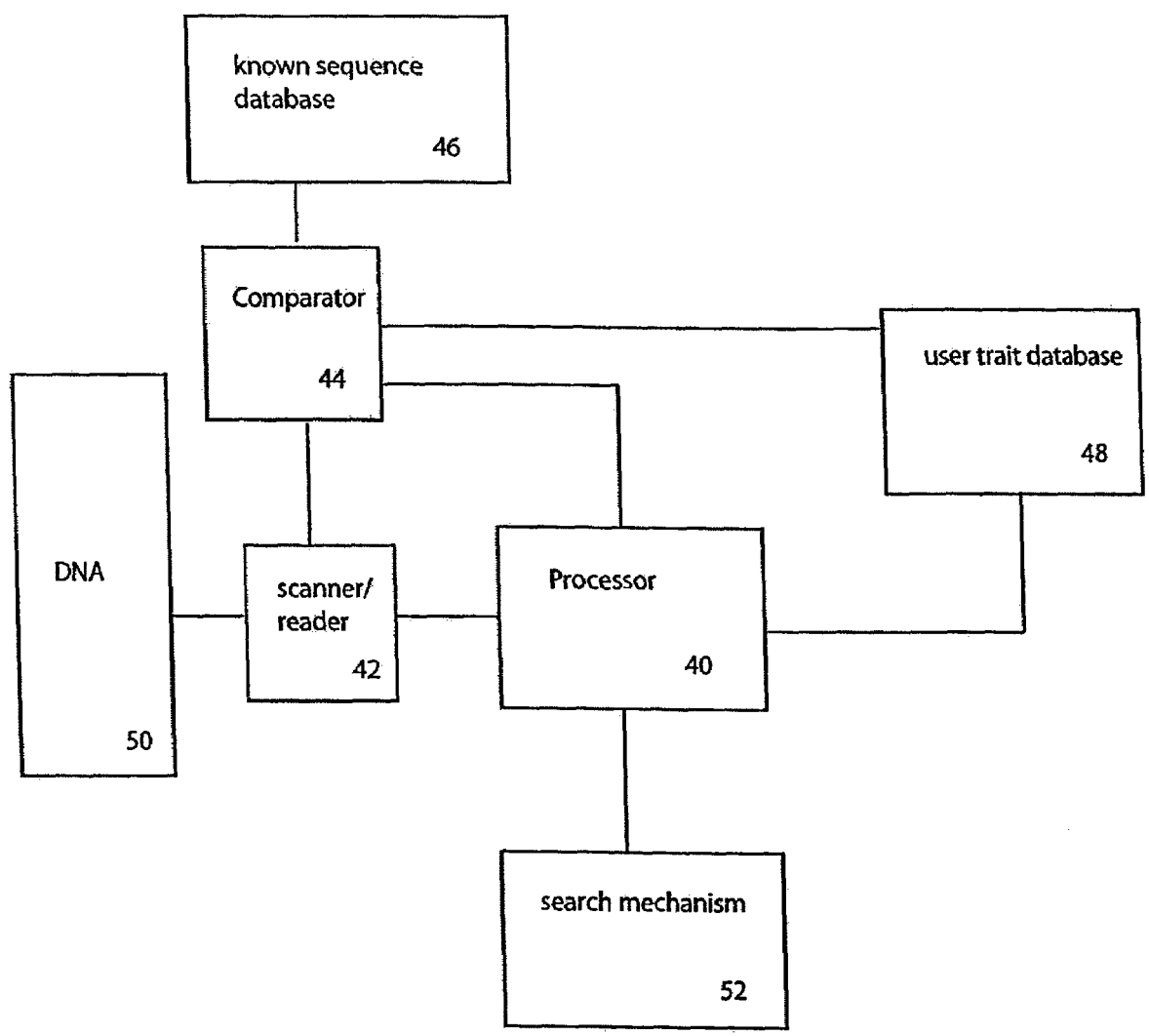
FIG. 4 is an illustrative view of the formation of a trait list from a sequence of DNA.

FIG. 4 is an illustrative view of the formation of a trait list from a sequence of DNA. The system 10 of the present invention includes a processor 40 having a DNA scanner/reader 42 connected thereto. The system further includes a comparator 44 connected to the processor 40 and between the scanner/reader 42 and a first database 46. The first database 46 includes information about DNA sequences and any phenotypic or genotypic traits that correspond to specific DNA sequences. The system 10 includes a second database 48 connected to the processor 40 and the comparator 44. The second database 48 is a user trait database and contains records representing users of the system 10. Each record contains a list of traits possessed by the respective user as well as the sequence of the users DNA.

In order for the system 10 to populate user records in the trait database 48, a user record must be created therein. The processor 40 creates a user record in the trait database 48. Thereafter the system 10 must analyze a sequence of DNA 50. The sequences to be analyzed will come from samples obtained in the method as discussed hereinabove with specific reference to FIGS. 1 and 2. The processor 40 directs the scanner/reader 42 to read the DNA sequence from the 5' end to the 3'. Upon reading the sequence 50, the scanner/reader 42 provides the sequence to the comparator 44. The processor 40 then directs the comparator 44 to compare the sequence 50 provided by the reader with all of the records in the known sequence database 46. Upon the comparator 44 determining a match between the sequence 50 and a known sequence, the processor 40 directs the comparator 44 to retrieve the trait corresponding to the known sequence. Thereafter, the processor creates a sub-record under the user record and inserts the trait as the value for that specific sub-record. This process is repeated until the entire sequence 50 is compared with all known sequences stored in the sequence database 46. The processor 40 also creates a sequence sub-record in the created user record in the trait database 48 and inserts the sequence 50 read by the scanner/reader 42 therein. Upon extrapolating all known traits from the sequence 50 and creating sub-records corresponding to each known trait under a created user record, the trait database is searchable via a search mechanism 52.

The search mechanism 52 is connected to the processor 40 and preferably a web-based search mechanism wherein a user can remotely log into the system 10 of the present invention. Upon logging in, the user can selectively search the trait database 48 as discussed hereinabove with specific reference to FIG. 3. Alternatively, the users may access the trait list of another user if the first user is aware of the other users member name. If the trait information is accessed using a known user name, the actual genetic code that corresponds to the traits is kept confidential. Furthermore, the searching user can utilize the user feedback system by entering at least one item of additional information that may be contained therein. The user feedback system includes a pre-determined questionnaire for eliciting additional information from the user. The responses given are stored in the user feedback database and each record is linked with the user's genetic information stored in the trait database so that, upon entering the at least one item of additional information, the search will retrieve the genetic information of additional users. However, it is important to note that the additional information obtained by the user feedback system is not used by the combination systems as discussed hereinafter with specific reference to FIGS. 5 and 7. The information stored in the user feedback database is merely an expanded search tool to be used by the users of the system 10 of the present invention. Therefore, when a user enters the at least one additional item of information, it does not necessarily mean that the V-child produced by the virtual combination system will possess the characteristic or trait corresponding to the at least one additional item of information. The traits of the V-child are solely determined by the virtual combination of the searching and matching user's genetic information.

Figure 5:
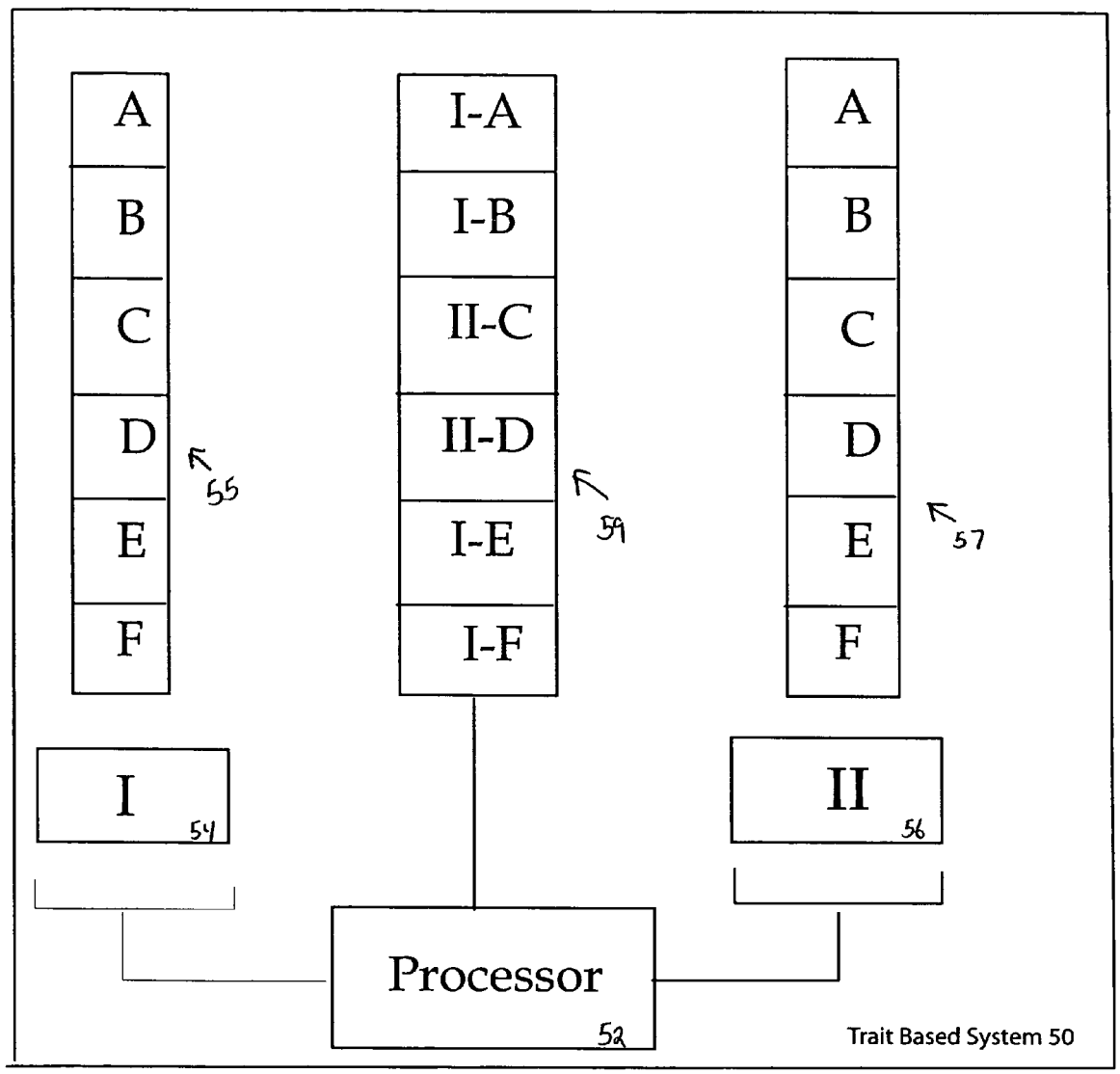
FIG. 5 is a block diagram of a combination system using trait lists for combining the genetic traits of two users to produce a virtual offspring.

FIG. 5 is a block diagram of a trait-based combination system 50 using trait lists for combining the genetic traits of two users to produce a virtual offspring. The trait-based combination system 50 includes a processor 52. As shown herein, the searching user 54 is represented with a roman numeral I. A matching user 56 is represented with the roman numeral II. Upon the searching user 54 selecting the matching user 56 to produce a virtual child therewith, the processor 52 retrieves the searching user's 54 trait list 55 from the trait database 48 as shown in FIG. 4. The processor 52 also retrieves a trait list 57 corresponding to the matching user 56. Each trait list 55, 57 includes a list of identified traits obtained from the sequence of DNA submitted to V-life for analysis. For purposes of example each trait list 55, 57 includes traits A-F. However, the trait lists 55, 57 may include any number of known traits. Additionally, the number of identified traits for the searching user 54 does not have to equal the number of identified traits for the matching user 56.

Upon the processor obtaining trait lists 55, 57 from the trait database 48, the processor 52 combines the searching user's 54 trait list with the matching user's 56 trait list. The combined list results in the processor 52 producing an offspring list 59. As shown herein, the offspring list 59 identifies which trait was inherited from which user. FIG. 5 shows that the offspring will possess traits A, B, E and F from the searching user (I) and traits C and D from the matching user (II). The mechanism by which the processor 52 produces the offspring list can be at least one of random combination or algorithmic combination. If the combination mechanism is random, then the processor picks at random which traits the offspring will possess. However, if the combination mechanism is algorithmic, the processor 52 contains a pre-stored algorithm which determines which trait is selected from which user. It is preferable that the algorithm is a computer software application containing genomic data derived from studies of population genetics in order to have a more realistic virtual combination. Specifically, the algorithm should contain a number of steps equal to the number of identified traits contained in the trait lists 55, 57. For each trait, the algorithm includes external factors such as dominance, recessiveness, randomness, and sex-linkage. These external factors are mentioned for purposes of example only and the algorithm is not limited to considering only these external factors. A pre-determined value less than 1 is assigned to each factor and is applied to the searching user's trait and the matching user's trait. The algorithm then sums the external factor values together and the trait of the user having the value closest to 1 is the trait which is selected by the combination mechanism to be provided to the offspring. This algorithmic combination system is described for purposes of example. However, any algorithm for accurately determining which trait to be expressed by an offspring may be used.

Figure 6:
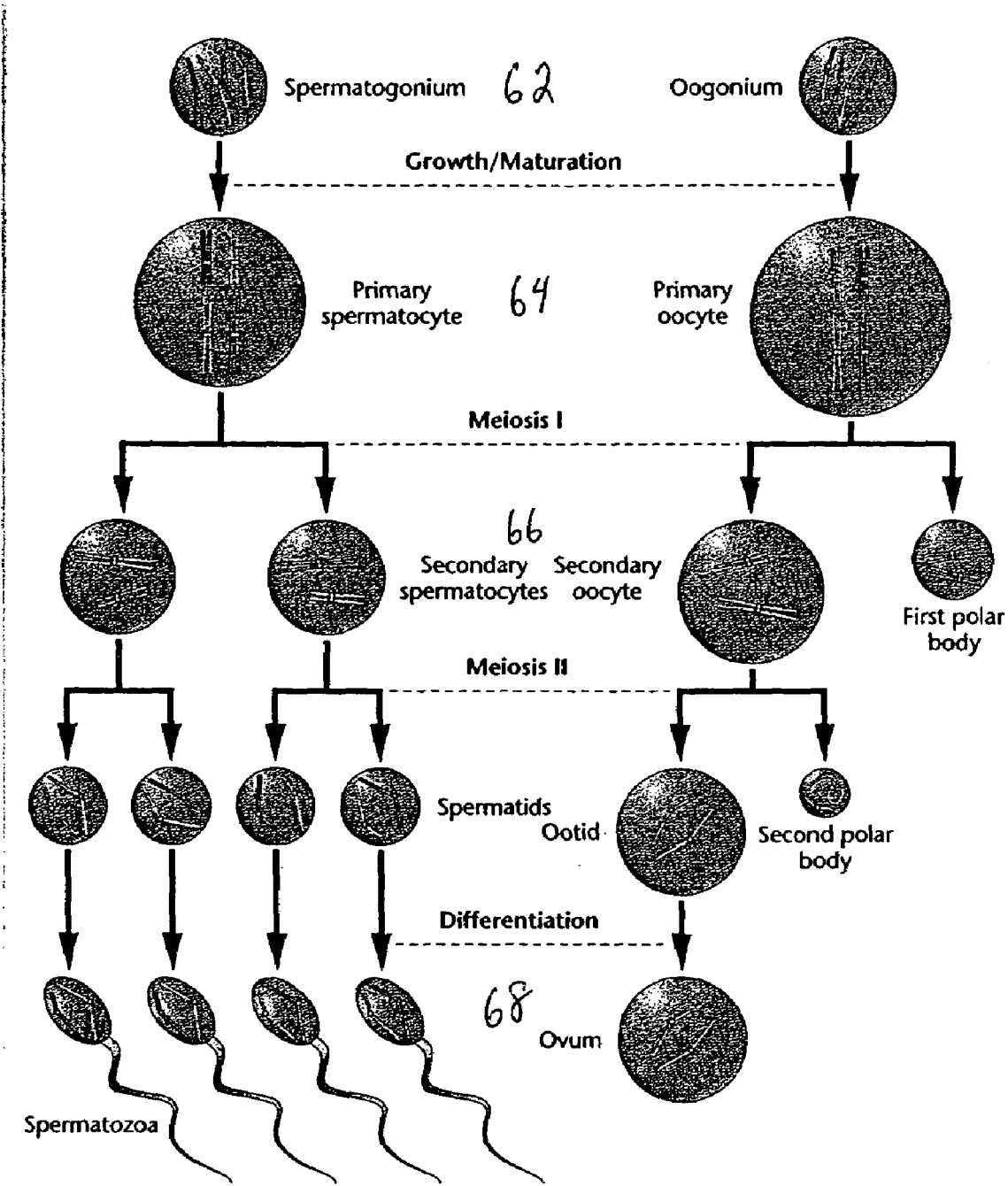
FIG. 6 is an illustrative view of an alternate embodiment of a combination system using virtual gametes produced from a virtual meiotic division.

FIG. 6 is an illustrative view of an alternate embodiment of a combination system using virtual gametes produced from a virtual meiotic division. Shown herein is a pictorial view of an algorithm to be stored in the processor 72 as shown in FIG. 7. The purpose of the meiotic division is to produce a cell that contains exactly half the genetic material that is required for a fully functional organism. Meiosis begins with a cell having a diploid number of chromosomes and results in a haploid gamete which has half the number of required chromosomes wherein the haploid cell has exactly one member of each homologous pair of chromosomes. Using a combination system that is based on a virtual meiotic division as shown here in FIG. 6 results in a more realistic combination of genetic material between the users as it allows for many unique combinations of maternally and paternally derived chromosomes.

The algorithm which controls the virtual gamete combination system used by the system 10 of the present invention virtually manipulates the genetic material to mirror the well known process of meiosis. As shown in FIG. 6, the DNA sequence obtained from the process discussed above with respect to FIG. 4 is used as a primary cell 62 for the virtual meiotic division. The first step in the algorithm requires manipulation of the genetic material using the steps of meiosis I to produce a replicated cell 64. The DNA of the replicated cell 64 is the same as the DNA of the primary cell 62 except that there are two copies of each homologous chromosome contained therein. Also included in this step is the process known as crossing over wherein genetic information contained in parts of the homologous chromosome pairs are exchanged. Thereafter, the DNA of each replicated cell 64 is split thereby producing a secondary cell 66. Each secondary cell 66 has the same amount of genetic material as the primary cell 62. The next step in the algorithm is to reduce the genetic information to the haploid number in order to produce gametes 68. It is important to note, as can be seen from FIG. 6, the reduction division discussed above produces a different number of gametes from the male users than from the female users of the system. In the male user, four (4) gametes are produced whereas the female user produces a single gamete (1). These gametes are then selected and combined as will be discussed below with specific reference to FIG. 7.

The above algorithm is described using cellular terminology for purposes of example only. However, no actual cellular manipulation occurs. Rather, the system 10 of the present invention utilizes the sequence of DNA obtained to produce a chromosomal map and chromosomes are manipulated using a computer software application so as to mirror the process of the meiotic division.

Figure 7:
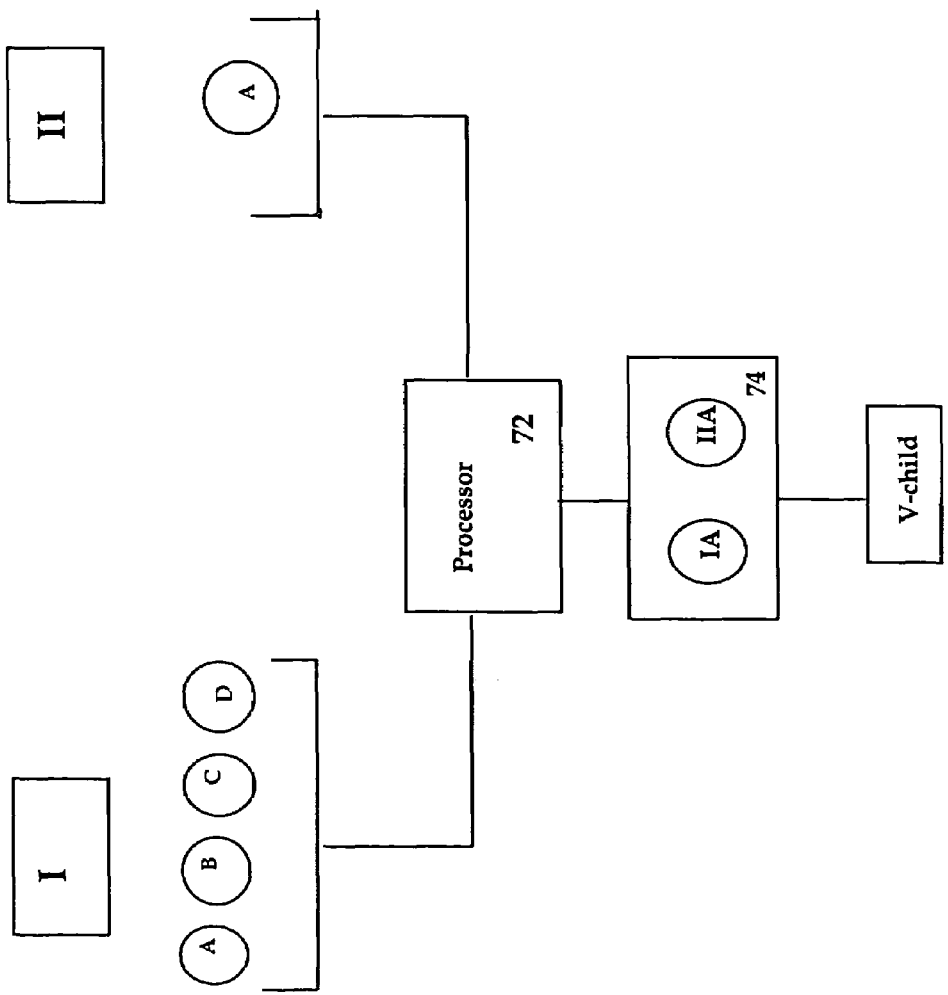
FIG. 7 is a block diagram of a combination system for producing virtual offspring using the virtual gametes produced from a virtual meiotic division.

FIG. 7 is a block diagram of a combination system 70 for producing virtual offspring using the virtual gametes produced from a virtual meiotic division. The virtual gamete combination system 70 includes a processor 72 for selectively combing the gametes of a first user (I) with a second user (II). For purposes of combining gametes as will be discussed hereinbelow, it is not relevant which user is the searching user and which user is the matching user. Additionally, for purposes of example only, the first user (I) is the male user and the second user (II) is the female user of the system. However, either user (I) or (II) could be either male or female. Using the virtual gamete combination system 70, it is important to know which user is male and which is female because the meiotic products of male and female gamete production differ in the number of gametes produced as discussed above with respect to FIG. 6. Formation of the male gamete result in four (4) potential gametes, represented by letters A-D, whereas formation of the female gamete results in only a single (1) gamete, represented by the letter A. The genetic selection is determined above in accordance with the virtual meiotic division in a manner which preferably mirrors actual production of gametes in human beings.

The processor 72 selectively chooses which of the male gametes (A-D) will be used for combination with the single female gamete (A). The selection process preferably mimics nature and is completely random. As shown in FIG. 7, the processor 72 selected gamete (A) of user (I) to be combined with gamete (A) of user (II). The combination of the gamete (IA) with the gamete (IIA) is performed in combination means 74. After the combination means 74 combines the gametes, a V-child 76 is produced.

The DNA of the V-child is then sequenced and a trait list is generated in a manner similar to the manner discussed in FIG. 4 thereby allowing the users (I) and (II) to know the traits that will be expressed by the V-child.

It is important to note that combination systems discussed hereinabove with specific reference to FIGS. 5-7, do not require the knowledge or consent of both parties in order for combination to occur. Preferably, the system 10 of the present invention is configured to allow production of a virtual child using the genetic material of two system users but only have one user aware of the creation of the virtual child. Alternatively, the system may be configured wherein the consent of both parties is required for mating to occur. This is a design feature and could also be an option that each user is able to select or deselect when registering to use the system. However, it is important to note that should only one user be part of the creation of a virtual child, the non-aware user's identification information is kept private. Also, the actual sequence that forms the genetic code is kept confidential so that the list of traits associated with the non-searching user is presented to the searching user. Further, as discussed above if a user is aware of another users member name, then that user is able to access the list of traits possessed by the user. While the trait list of the user is accessible, the corresponding genetic code is kept confidential along with the personal identification of the user.

Figure 8:
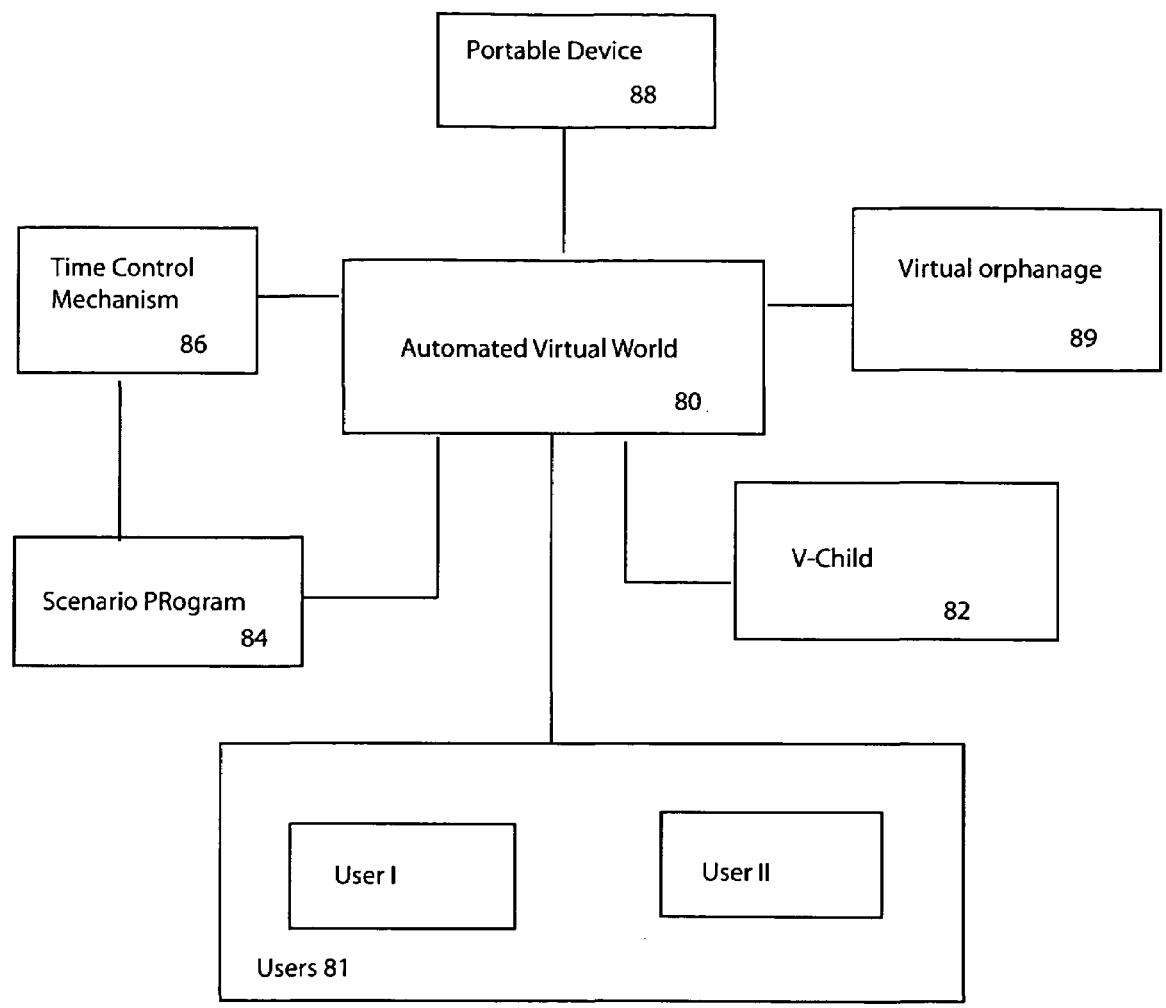
FIG. 8 is a block diagram of a fully automated virtual world.

FIG. 8 is a block diagram of a fully automated virtual world 80, hereinafter the automated world. The automated world 80 includes user (I), user (II), collectively known as users 81 and the V-Child 82. The automated world further includes a plurality of pre-programmed scenarios 84 that form the rules of the automated world 80. A selectively controllable time control mechanism 86 is also part of the automated world and is connected to the scenarios 84.

Upon creation of a virtual child 82, the users (I) and (II) can selective raise the virtual child 82 in the automated world. In the automated world 80, the only active participants are the users 81. The V-Child is shown with the combined genetic material from the users 81 and is able to respond to commands given thereby. Additionally, the V-child 82 is responsive to the scenarios 84. The users 81 are guided by the rules of the scenarios 84 and raise the V-child 82. The users 81 are able to selectively control the time-flow their particular automated world with the time control mechanism 86. The users 81 determine the unit of time and thus can determine how fast their V-child 82 matures. This time control mechanism 86 is selectively adjustable at any time after the automate world 80 is joined by the users.

Should the users 81 desire to constantly monitor the actions of their V-child 82, a portable device 88 is selectively connected to the automated world 80. The portable device includes at least one of a PDA, a laptop computer and a wrist watch. The automated world 80 is selectively downloadable onto the portable device 88 and the users 81 are able to continue raise the V-child 82 using the portable device 88. This is ideal when the users 81 know they will not be able to log into the system 10 of the present invention. Additionally, the portable devices 88 of both users can be connected to each other so that both V-parents are able to facilitate the interaction and development of the V-child 82 when both users are offline. The manner in which the portable devices 88 are connected to one another includes at least one of a serial connection, a USB connection, an infra-red (IR) connection and a firewire connection.

Furthermore, should the users 81 decide they no longer want to raise the virtual child 82, the virtual child 82 can be deposited into a virtual orphanage 89. The virtual orphanage 89 functions like an auto-pilot wherein a time unit is selectively determined and the V-Child 82 is raised by pre-stored instructions in the scenarios 84. The life of the V-child lasts until, an end scenario is selected by the automated world 80. Alternatively, once a V-child is deposited into a virtual orphanage 89, other users may be able to access that particular automated world. If an outside user(s) decides to access the automated world, that outside user (s) can selectively determine if they want to continue raising the V-child from that point in time. Should this be decided, the outside user is granted full control over the automated world 80. Further, the outside user(s) are prohibited from knowing who the original users 81 were and are limited to knowing the genetic makeup of the V-child 82.

Since this is an automated world and the only participants are the users, the system of the present invention preferably includes means for storing a plurality of automated worlds that each operates independent of one another.

Figure 9:
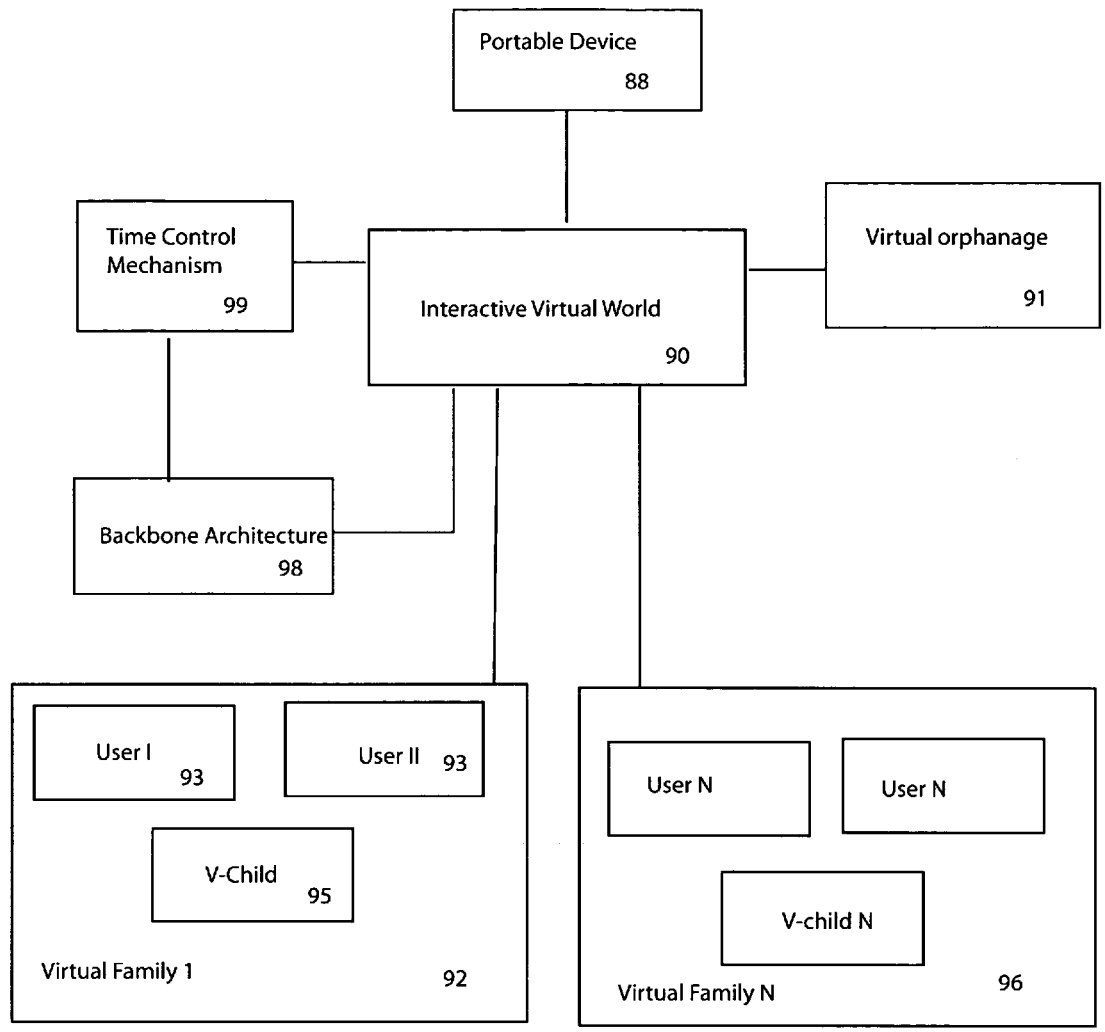
FIG. 9 is a block diagram of an interactive virtual world.

FIG. 9 is a block diagram of an completely interactive virtual world 90, hereinafter known as the interactive world 90. The interactive world 90 includes a first virtual family 92 and virtual family N 96, wherein N represents the number of virtual families participating in the interactive world 90. Each virtual family 92, 96 includes at least one virtual parent 93 and a virtual child 95. The interactive world 90 is controlled by backbone architecture 98 and a timing mechanism 99. The backbone architecture is preferably a software program that defines general rules for the interactive world 90. Preferably, the backbone architecture provides a wide open virtual world that is completely interactive such that all virtual parents are able to interact with one another as well as with each virtual child. Furthermore, the virtual children are able to interact with all of the virtual parents as well as the other virtual children. The virtual parents of each respective virtual child are able to control and raise their respective virtual child. Thus, the interactive world 90 simulates the process of raising a child such that there are influences outside of the virtual parents that affect how the virtual child is raised. Furthermore, the backbone architecture includes scenarios including but not limited to day care, school, college, work environment. However, the backbone architecture can be programmed to simulate any real world situation thereby providing the users (virtual parents 93) with a realistic simulation in which to raise their virtual child 95 which was formed from a virtual combination of the users 93 actual genetic material.

The timing mechanism 99 is unlike the timing mechanism as described above in FIG. 8. Specifically, in the interactive world, since there are multiple participants, a unit of time must remain constant for all users. The timing mechanism 99 is selectively programmed prior to the interactive world 90 being inhabited by users and virtual children. However, the system 10 may include a plurality of interactive worlds 90 each having a timing mechanism 99 set to proceed at a different speed so as to give the users of the system 10 the choice as to how they want to participate in raising their virtual children.

Similar to the automated world 80 in FIG. 8, the interactive world includes a virtual orphanage 91. This allows users 93 who no longer want to partake in the interactive world 90 to deposit their virtual child 93 therein. Upon a virtual child 93 being deposited in the virtual orphanage 91, the virtual orphanage 91 functions similar to the virtual orphanage 89 of the automated world 80 discussed above with respect to FIG. 8. However, since this is the interactive world 90, the children in the virtual orphanage 91 are accessible by at least one of a participant of the interactive world 90 and non-participant of the interactive world 90. Should a non-participant desire to take over raising the virtual child, the users status is changed from non-participant to participant of that particular interactive world 90.

The description of both the automated world 80 in FIG. 8 and the interactive world 90 in FIG. 90 is for purposes of example only. Each world 80, 90 can be selectively programmed to operate and function in any desired manner.

A further aspect of the present invention is to allow the V-children produced from the users genetic and trait information to mate in a similar manner as the V-parents. This option is available in each of the fully automated and interactive worlds (collectively, worlds). As the V-children develop and are raised by their V-parents, the worlds can selectively cause the multiple V-children present in each world to mate with one another. This process allows for at least one of the trait based information or actual genetic code of a first v-child to be combined with that of a second v-child. Thereafter, the V-parents will not only have V-children, but v-grandchildren. Further application of this option is to create extended V-families and communities. The manner in which the V-children mate with one another is similar to the manner in which the V-parents are mated which is discussed hereinabove with specific reference to FIGS. 2-7.

From the above description it can be seen that the present invention overcomes the shortcomings of the prior art by providing a system and method for matching users qualities and traits obtained from submitted DNA samples. The system includes a cotton swab for swabbing the inside of the user's mouth in order to obtain a DNA sample and a transport kit for transporting the swab to a lab for DNA analysis thereof. Each submitted DNA sample is sequenced and a list of traits and characteristics is produced. Users can input specific characteristic which a desired mate should possess and the system can search the catalogued DNA samples for a potential match. Upon a user determining that a selected sample is acceptable, the system virtually combines the users DNA with the selected DNA in order to produce a virtual child. The system then allows the user(s) to raise the virtual child in at least one of real time and accelerated time. The virtual child can be transported on any portable electronic device and should the virtual child no longer be desired, the virtual child can be placed in a virtual orphanage. Other users can then choose to adopt any of the virtual children stored in the virtual orphanage. The user can also selectively choose to meet the actual person whose DNA sample was combined with the users.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. A computer implemented system for producing virtual offspring comprising:
    a) a source of genetic material physically acquired from a plurality of different users;
    b) an analysis processor for analyzing said acquired genetic material for determining at least one trait corresponding to said genetic material;
    c) a user database electrically coupled to said analysis processor for storing user data representing said at least one trait for each respective one of said users;
    d) a search mechanism electrically coupled to said analysis processor for enabling said at least one user to input data representing a desirable trait and search said user data stored in said user database for users having said at least one desirable trait and retrieve data representing users having said at least one input desirable trait; and
    e) a combination processor, electrically coupled to said search mechanism and said user database for combining data representing a sample of genetic material from a first user with data representing a sample of genetic material of a selected second user including said at least one input desired trait for producing data representing an offspring of said first and second user, said combination processor combines data representing said genetic material from said first user with data representing a selected one of said users having said at least one input desired trait to output data representing an offspring including data representing genetic material from each of said first and second users, said data representing an offspring being displayed on a display device.

2. The system as recited in claim 1, wherein said source of genetic material is populated by a kit that is selectively received by a user, said kit comprises:
    a) a swab having a cotton tip at a distal end thereof for rubbing along an inner side of a user's cheek and retaining epithelial cells thereon;
    b) a selectively sealable vile for receiving said cotton tip therein; and c) means for transferring said selectively sealable vile having said cotton tip therein to a remote location, wherein upon receipt of said vile, genetic material is eluted from said epithelial cells retained on said tip.

3. The system as recited in claim 1, wherein said acquired genetic material is DNA.

4. The system as recited in claim 3, wherein said analysis processor includes:
   a) a DNA sequencer for sequencing said acquired DNA;
   b) a second database having data representing previously identified traits that correspond to particular DNA sequences stored therein; and
   c) a comparator for receiving said sequenced acquired DNA and comparing said received sequence with said known sequence data stored in said second database, and upon said comparator determining that said received sequence matches a respective one of said known sequence, said comparator provides said previously identified trait corresponding to said known sequence to said user database for storage therein.

5. The system as recited in claim 4, wherein said user database includes a unique record representing each respective user of said system, and each unique record includes at least one sub-record for storing data representing said at least one previously identified traits.

6. The system as recited in claim 5, wherein said second database is selectively updateable to include previously unknown traits that correspond to DNA sequences.

7. The system as recited in claim 6, wherein said analysis processor re-analyzes said data representing acquired DNA at pre-determined intervals for determining if said sequence corresponds to a sequence of a previously unknown trait, said analyzing means selectively updates said user database upon completion of said re-analyzing.

8. The system as recited in claim 1, wherein said search mechanism is a web-based search tool using at least one of a keyword search and a Boolean search technique.

9. The system as recited in claim 1, wherein upon said at least one trait being identified and stored in said user database, said user database produces a trait list having all identified traits for each user.

10. The system as recited in claim 9, wherein said combination processor retrieves said trait lists from said user database for each one of said users whose genetic material is to be combined and combines data representing said user trait lists into an offspring trait list using a combination algorithm.

11. The system as recited in claim 10, wherein said combination algorithm selectively determines which trait from each of said user trait lists will be present in said offspring trait list, said combination algorithm includes a plurality of external factors associated with each respective one of said traits in said trait lists and assigns a numerical value to each respective external factor for summation thereof, the trait present in said offspring list is the trait in the user list having the highest sum of external factors.

12. The system as recited in claim 11, wherein external factors include dominance, recessiveness, randomness, and sex-linkage.

13. The system as recited in claim 9, wherein said analysis processor analyzes said data representing acquired genetic material to derive data representing a chromosomal map for each respective user and derive data representing gametes from said chromosomal map using a meiotic division algorithm.

14. The system as recited in claim 13, wherein said meiotic division algorithm manipulates said chromosomal map data to undergo a meiotic division by manipulating said chromosomal map data through all phases of a meiotic division.

15. The system as recited in claim 1, further comprising a user feedback processor enabling a user to input user feedback data representing at least one characteristic of said user.

16. The system as recited in claim 15, wherein said at least one characteristic is at least one of physical characteristics, mental characteristics, emotional characteristics, talents, likes and dislikes of said respective user.

17. The system as recited in claim 15, wherein said search mechanism allows users to search at least one of said stored user data and said user feedback data to obtain a list of users having at least one of a desired trait and a desired characteristic.

18. The system as recited in claim 1, further comprising a modification processor conditioned to selectively modify data representing said offspring using time-dependent instructions to selectively modify said offspring data being output on said display.

19. The system as recited in claim 18, further comprising a database for receiving data representing said offspring, and wherein said processor automatically implements an algorithm for modifying offspring data according to said time dependent instructions.

20. The system as recited in claim 18, further comprising a portable communication device selectively communicating with said processor for selectively modifying said offspring data and enabling said users to input instructions for modifying said offspring data using said portable device.

21. The system as recited in claim 1, further comprising a probability processor for determining a probability that a trait possessed by one of said first user and said selected one of said users will be expressed in said virtual offspring.

22. A method implemented by a computer processing device for matching users with one another comprising the steps of:
   a) physically acquiring genetic material from users;
   b) analyzing the acquired genetic material for determining at least one trait corresponding to the genetic material using an analysis processor;
   c) storing user data representing the at least one trait for each respective ones of the users in a user database electrically coupled to the analysis processor;
   d) searching the user database for users having at least one desirable trait in response to user input data representing a desirable trait and retrieving data representing users having said at least one input desirable train with a search mechanism electrically coupled to the analysis processor and the user database;
   e) combining data representing a sample of genetic material from a first user with data representing a sample of genetic material of a selected second user including said at least one input desired trait for producing data representing an offspring of said first and second user including data representing genetic material from each of said first and second users; and
   f) displaying data representing the offspring on a display device.

23. The method as recited in claim 22, further comprising the step of raising the virtual offspring produced by said combining step in at least one of an automated world and an interactive world.

* * * * *